(12) United States Patent
Shah et al.

(10) Patent No.: US 6,280,634 B1
(45) Date of Patent: Aug. 28, 2001

(54) METHOD OF DETERMINING SYSTEM VOLUME OF A DIALYSIS MACHINE

(75) Inventors: Dilip H. Shah, Buffalo Grove; Derek Wiebenson, Palatine; Tom L. Brose, Gurnee; Shincy Maliekkal, Mr. Prospect, all of IL (US)

(73) Assignee: Aksys Ltd., Lincolnshire, IL (US)

( * ) Notice: Subject to any disclaimer, the term of this patent is extended or adjusted under 35 U.S.C. 154(b) by 0 days.

(21) Appl. No.: 09/590,812

(22) Filed: Jun. 9, 2000

Related U.S. Application Data

(60) Division of application No. 09/186,501, filed on Nov. 4, 1998, now Pat. No. 6,136,201, which is a continuation-in-part of application No. 08/762,072, filed on Dec. 9, 1996, now Pat. No. 5,932,110.

(51) Int. Cl.[7] ............... B01D 61/26; B01D 61/28; G01F 13/00; G01F 22/00
(52) U.S. Cl. ............ 210/739; 210/646; 210/647; 210/746; 73/861.08
(58) Field of Search .................. 210/646, 647, 210/739, 746; 73/861, 861.08

(56) References Cited

U.S. PATENT DOCUMENTS

| | | | |
|---|---|---|---|
| 4,734,198 | * 3/1988 | Harm et al. | 210/647 |
| 5,015,389 | 5/1991 | Portillo, Jr. | 210/646 |
| 5,024,756 | 6/1991 | Sternby, Jr. | 210/93 |
| 5,091,094 | 2/1992 | Veech | 210/647 |
| 5,244,568 | 9/1993 | Lindsay et al. | 210/87 |
| 5,247,434 | 9/1993 | Peterson | 210/646 |
| 5,336,165 | 8/1994 | Twardowski | 210/636 |
| 5,344,231 | 9/1994 | Jönsson et al. | 366/137 |
| 5,348,389 | 9/1994 | Jönsson et al. | 366/136 |
| 5,591,344 | 1/1997 | Kenley et al. | 210/636 |
| 5,932,110 | 8/1999 | Shah et al. | 210/739 |

FOREIGN PATENT DOCUMENTS

| | | |
|---|---|---|
| 2446075 | 4/1975 | (DE) . |
| 8305713 | 12/1985 | (DE) . |
| 2212164 | 7/1994 | (FR) . |

\* cited by examiner

Primary Examiner—John Kim
(74) Attorney, Agent, or Firm—McDonnell Boehnen Hulbert & Berghoff

(57) ABSTRACT

A method of calibrating a dialysis machine to determine the volume of a dialysate flow path of the machine including a dialysate preparation tank includes the steps of introducing a known quantity of electrically conductive chemicals into the dialysate preparation tank, filling the dialysate solution flow path with water, mixing the chemicals with water to form a solution, measuring the conductivity of the solution, calculating the system volume ($V_{sys}$) according to the relation: $V_{sys} = M/(a_1 r + b_1)$ where M is the mass in grams of the chemicals, $a_1$ and $b_1$ are a coefficient of linearity and a constant of linearity, respectively, for the chemicals and r is the measured conductivity of the solution.

4 Claims, 4 Drawing Sheets

METHOD OF DETERMINING SYSTEM VOLUME OF A DIALYSIS MACHINE

CROSS-REFERENCE TO RELATED APPLICATION

This is a divisional of application Ser. No. 09/186,501 filed Nov. 4, 1998, U.S. Pat. No. 6,136,201 which is a a continuation-in-part of application Ser. No. 08/762,072 filed Dec. 9, 1996, U.S. Pat. No. 5,932,110.

BACKGROUND OF THE INVENTION

A. Field of the Invention

This invention relates generally to machines that are used to prepare a physiological solution from a batch of chemicals, such as dialysis machines, including peritoneal and hemodialysis machines. More particularly, the invention relates to the process by which the solution is prepared and the conductivity of the solution is adjusted. The invention is particularly useful in conjunction with a machine that prepares and stores an entire batch of solution, such as a batch dialysate preparation system for a dialysis machine, as opposed to machines based on so-called "proportioning" systems, in which the solution is prepared continuously during the treatment session.

B. Statement of Related Art

Dialysis, including hemodialysis and peritoneal dialysis, is a treatment for patients that suffer from inadequate kidney function. In hemodialysis, blood is pumped from the patient's body through an extracorporeal artificial kidney circuit to a dialyzer. Blood-borne toxins and excess water are filtered out of the blood through a semipermeable dialyzer membrane into an electrolyte (dialysate) solution. In peritoneal dialysis, the patient infuses a quantity of dialysate into the peritoneal cavity, and the peritoneal membrane acts as the semipermeable membrane. After a dwell period, the dialysate fluid is drained and a fresh supply of peritoneal dialysate is added to the peritoneal cavity.

The dialysate solution used in hemodialysis and peritoneal dialysis machines has typically been prepared using a proportioning technique, wherein a concentrated dialysate solution is mixed with water to form a dialysate solution with the aid of a proportioning pump. To control the dialysate conductivity in a proportioning system, the proportioning pump is precisely regulated, or alternatively, the rate of supply of the dialysate powder and water to a mixing vessel is regulated. A representative dialysis machine that uses precise control of proportioning pumps is described in the Peterson et al. patent, U.S. Pat. No. 5,247,434.

In a batch system, unlike a proportioning system, an entire batch of dialysate (e.g., approximately 50 liters) is prepared shortly before the dialysis session and stored in a dialysate solution tank. See the patents to Kenley et al., U.S. Pat. No. 5,591,344, and Twardowski, U.S. Pat. No. 5,336,165 for descriptions of representative batch systems. Batch dialysate solution is typically prepared from a powdered sodium bicarbonate formulation and a liquid acid concentrate that are added to the dialysate solution tank and mixed to water to form an approximately 50 liter batch. The dialysate powder and liquid acid formulations may be stored in individual containers during shipping, and are opened at the time of preparation of the solution and their contents added to the tank.

Since the total volume of the dialysate tank and associated dialysate fluid circuits is reasonably constant and capable of being determined experimentally, one method of insuring that the concentration and conductivity of the resulting dialysate solution is accurate is to precisely control the quantity and formulation of the dialysate concentrates that are used to make up each batch of dialysate. This method would work if it were possible to also precisely control the total fluid volume of the dialysate fluid circuit including the dialysate tank.

In practice, the above method has disadvantages. First, precise control of the quantity and formulation of the dialysate concentrates in their individual vessels is difficult and expensive. Additionally, the total fluid volume of the dialysate circuit and tank can vary due to manufacturing tolerances and changes in components over the life cycle of the dialysis machine. If the tank and associated dialysate fluid circuit are subject to heat disinfection cycles, this can cause a slight expansion of the components resulting in an increase in system volume. It has been determined that even small fluctuations in total system volume can cause conductivity measurements that are out of a desired range, unless the quantity of the bicarbonate and liquid acid concentrates added during the preparation of the batch of dialysate are precisely controlled.

The present inventors have further appreciated that the process of preparing a batch of dialysate solution has its own difficulties, including the instability of the solution during the process of mixing the solution, the possibility of loss of carbon dioxide gas from the bicarbonate solution and resulting precipitation of calcium carbonate in the dialysate tank, and a substantial amount time being required to thoroughly mix a batch quantity of solution automatically in a compact machine suitable for use in environments outside of traditional dialysis clinic settings. The present invention describes methods of preparing the batch dialysate solution that overcome these and other difficulties.

SUMMARY OF THE INVENTION

A method is provided for preparing a batch of physiologic solution from batch quantities of first and second chemical formulations stored in respective first and second batch quantity chemical vessels. The method comprises the steps of opening the first batch quantity vessel (e.g., a vessel containing a liquid acid formulation) and placing the first chemical formulation in a solution preparation tank. Then, the first chemical formulation is removed from the solution preparation tank and sequestered elsewhere within the system, such as in an auxiliary tank such as an ultrafiltration tank in a hemodialysis embodiment. The first chemical formulation is then preferably diluted, such as by adding a few liters of water to the place where the chemical formulation is sequestered.

Then, the second batch quantity vessel is opened, and the second chemical formulation stored therein (e.g., a bicarbonate formulation) is introduced into the solution preparation tank. The second chemical formulation is diluted with water. During this process, the first chemical formulation (e.g., liquid acid) remains sequestered from said second chemical formulation.

Then, the dilute solution of the second chemical formulation is mixed with the first chemical formulation to form a physiologic solution and the resulting solution is stored in the dialysate solution tank.

The above mixing procedure has some advantages and avoids some of the problems that can arise when a physiologic solution is being prepared from acid and bicarbonate components. With the above method, the bicarbonate is fully dissolved before the liquid acid solution is mixed with the bicarbonate solution. If you were to add the liquid acid when the bicarbonate is not fully dissolved or is highly concentrated, the resulting solution is unstable and loss of carbon dioxide gas from the tank can produce calcium precipitation at the bottom of the tank. Further, the above procedure can shorten the total amount of time required to prepare the physiologic solution.

The physiologic solution prepared in accordance with the above process could be any pertinent physiologic solution, such as a dialysis solution (hemodialysis or peritoneal), a substitution fluid, or a surgical or irrigation fluid.

Additionally, the method may continue with the step of diluting the resulting physiologic solution with a predetermined amount of water to form a final physiologic solution having a desired conductivity level. The predetermined amount of water may be determined from a known system volume and a conductivity measurement of the prepared physiologic solution. The system volume may also be calibrated at the factory or in the field using techniques described herein.

BRIEF DESCRIPTION OF THE DRAWINGS

Presently preferred embodiments of the invention will be described below in conjunction with the appended drawings in which like elements refer to like elements in the various views, and in which.

DETAILED DESCRIPTION OF THE PREFERRED AND ALTERNATIVE EMBODIMENTS

Figure 1:
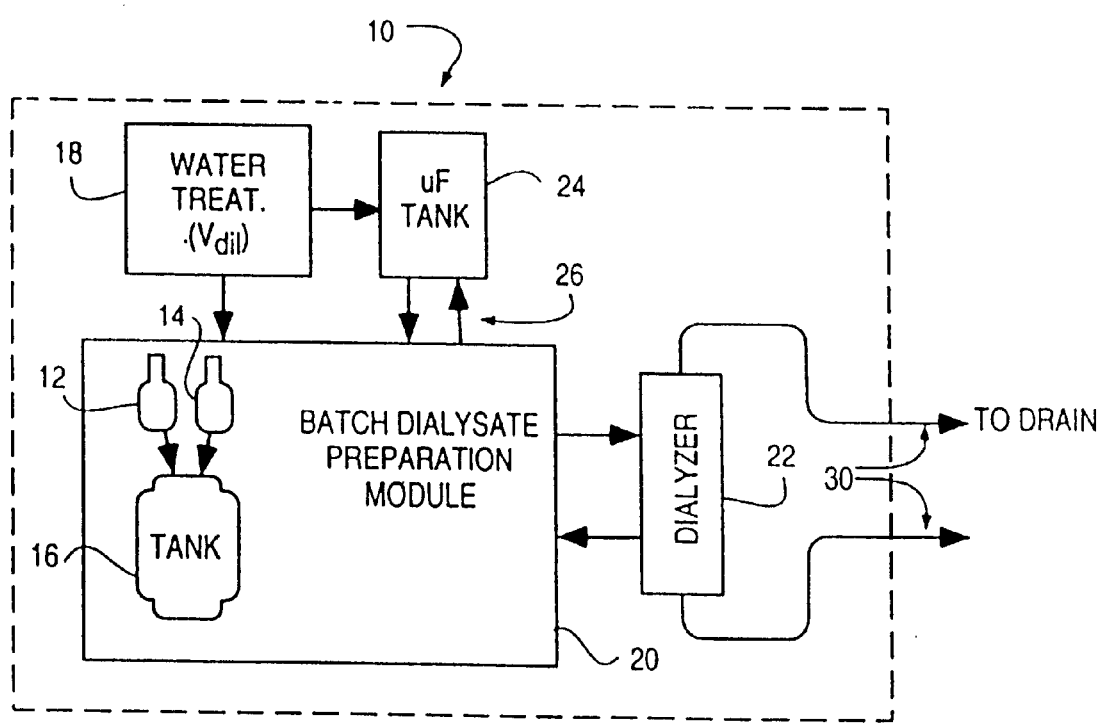
FIG. 1 is a simplified schematic representation showing the structures used to perform the solution preparation method according to a preferred hemodialysis embodiment of the invention.

Referring to FIG. 1, the preferred embodiment of the present invention is used in conjunction with a dialysis machine 10 that prepares a batch of dialysate. To prepare the batch of dialysate, two batch quantity chemical vessels 12, 14 are provided that store a concentrated bicarbonate powder formulation and a liquid acid concentrate, respectively. In one embodiment, at the time of preparation of the dialysate, the vessels 12, 14 are opened and their contents dispersed into a dialysate preparation tank 16. The tank 16 is then filled with reverse-osmosis filtered water from a water preparation and treatment module 18 or equivalent supply means. The resulting solution is mixed by circulation in a closed loop in a batch dialysate preparation module 20, for example by swirling action in the tank 16, withdrawal of the solution from the bottom of the tank 16 and reintroduction of the solution into the top of the tank 16.

The total volume of the dialysate fluid circuit path in module 20 including the tank 16 and associated tubing in the dialysate circuit will be known and experimentally determined at the time of manufacture of the machine 10. Given the expected total system volume, a target or desired quantity of dialysate chemicals for the two vessels 12, 14 can be calculated for a solution with a desired conductivity level. One method of determining the system volume is to prepare a batch of dialysate from a precisely known quantity of chemicals, measure the conductivity, and calculate the volume of fluid needed to produce the measured conductivity given the amount of chemicals added to the dialysate preparation tank.

In accordance with one embodiment, we add approximately 5%–7% excess bicarbonate and liquid acid chemicals to the two vessels 12, 14 (above the desired or target quantity). A suitable range of excess chemicals is presently contemplated at being between about 3% and 7% of normal, depending on the tolerance in the filling of the vessels, the amount of wasted dialysate chemicals one is willing to endure, and other factors. In the examples where the manufacturing variation of the filling of dialysate chemicals in the vessels 12, 14 is +/−5% of the target, the variation will be shifted upwards to a range of between 0% and 10% of the target if 5% excess is added to the vessels. Preferably, the vessels are overfilled such that the resulting conductivity of the batch of dialysate is always at least equal to a target or desired conductivity level.

After the dialysate chemicals are mixed in the tank 16 and circulated through the dialysate flow path in module 20, a dialyzer clearance test is performed. This is performed by circulating dialysate on one side of the dialyzer 22 membrane and circulating water on the blood side of the dialyzer 22. At this time, a separate measurement of the conductivity of the batch dialysate is taken, the quantity $\sigma_{mas}$ in the equations set forth below. Based upon the predetermined average system volume, the measured conductivity, and the desired conductivity of the dialysate, a calculation (described below) is made of the volume of water to be added to the dialysate solution to dilute the solution down to the desired conductivity level. This calculation is made by a suitable microprocessor or computer controlling the dialysis machine 10.

In one embodiment, this calculated volume of water is added to an ultrafiltration (UF) tank 24 from the water preparation and treatment module 18 or equivalent supply source. The UF tank 24 is in fluid connection with dialysate solution flow path in the dialysate preparation module 20. The dialysate is pumped through the ultrafiltration tank (represented by arrows 26 in FIG. 1), where it mixes with the water. A period of mixing occurs, for example, 40 minutes, during which time the water in the ultrafiltration tank 24 is thoroughly mixed with the dialysate and the dialysate solution is fully diluted down to the proper conductivity level.

In a volumetrically closed system, such as is the case in the preferred hemodialysis embodiment of the invention, the introduction of additional water into the dialysate flow path must be accompanied by a removal of the same amount of dialysate from the system. This can be accomplished by simply pumping a portion of dialysate equal to the volume of introduced water through a valve to a drain. However, the dialysate that is being evacuated from the system is a physiologic solution, and can be put to specific purposes, such as rinsing the extracorporeal blood tubing. In a preferred embodiment, we direct the dialysate through the membrane of the dialyzer 22 into the arterial and venous blood tubing set 30. The fluid exits the blood set 30 via a port apparatus connected to the arterial and venous lines (not shown in FIG. 1) and then to drain. In the process, pyrogens or other substances in the arterial and venous lines 30 are flushed from the blood tubing set.

A preferred embodiment of the above technique takes advantage of the storage capacity of the ultrafiltration tank 24. As noted above, to dilute the dialysate, the calculated volume of water is added to the ultrafiltration tank, 24, and the dialysate solution in the dialysate flow path in module 20 is pumped through the ultrafiltration tank 24, thereby mixing with the water. After a mixing period, e.g., 40 minutes, the dialysate fluid flow path is filled with dialysate and an excess quantity of dialysate is present in the ultrafiltration tank 24. This dialysate is then pumped through the dialyzer 22 and arterial and venous lines 30 and then to drain, and in the process rinsing the arterial and venous lines 30.

In a dialysis machine that is not a volumetrically closed system, such as a peritoneal dialysis machine, the extra dialysate can simply remain in the batch dialysate tank 16, or elsewhere in the flow path.

CALCULATION OF DILUTION VOLUME

The dialysis machine 10 further includes a host central processing unit or computer (not shown in the drawings) that governs operation of the machine, such as the host CPU described in the above-cited Kenley et al. patent, U.S. Pat. No. 5,591,344. A central computer control of a dialysis machine is well known in the art. The host CPU calculates the volume of water needed to dilute the dialysate solution. The equation for volume dilution is derived from the following relationship:

$$\sigma = a\, I + b \quad (1)$$

where $\sigma$+conductivity in mS/cm

I=total ionic strength in mEq/l a=coefficient of linearity b×constant of linearity, determined experimentally for a particular dialysate formulation.

This equation (1) is found to work within a 10% range of the desired concentration for any specific dialysate formulation. The regression coefficient is better than 99.9%. Also, when a higher concentration of dialysate is diluted to lower concentration by addition of reverse osmosis ("RO") water which has very low conductivity (less than 0.1 mS/cm), the resulting solution has all of its constituents proportionally lowered in equal percentages.

Each dialysate formulation conductivity can be experimentally and theoretically derived and will be termed "desired conductivity, $\sigma_{des}$." Similarly, $I_{des}$ is the desired ionic strength. Applying equation (1) to the desired formulation we get, $$\sigma_{des} = a\, I_{des} + b \quad (2)$$

Applying equation (1) to a measured bulk formulation before dilution we get, $$\sigma_{mas} = a\, I_{mas} + b \quad (3)$$

The quantity $\sigma_{mas}$ will vary from batch to batch after dilution with water due to the varying quantity of chemicals in the vessels 12, 14, and is measured by a conductivity cell in the dialysate flow path after the dialysate solution is mixed. Also, overall mass balance applied to the total dialysate fluid system yields the following result:

$$V_{sys} \cdot I_{mas} = (V_{sys} + V_{dil})\, I_{des} \quad (4)$$

where $V_{sys}$=Total system volume (without UF tank)

$V_{dil}$=Volume for dilution to be added to the dialysate (e.g., added to UF tank 24) Solving equations (2), (3) and (4) for dilution volume yields, $$V_{dil} = (V_{sys})(\sigma_{mas} - \sigma_{des})/(\sigma_{des} - b) \quad (5)$$

Thus, equation (5) gives the total volume of water needed to dilute the batch of dialysate to the desired conducting level. A variant on the above method is to account for the conductivity of the RO water used for dilution, $V_{dil}$. Although the RO water ($V_{dil}$) can contribute up to 0.1 mS/cm, its effect on 13–15 mS/cm fluid is 100 times less. Also, the impact of lesser concentration on conductivity is much higher, reducing the impact to 200 to 300 times less. Thus, accounting for RO conductivity in $V_{dil}$ in (5) would only need to perform where extraordinarily precise control of conductivity is required, and where the properties of the local water supply are known in advance. Also, in the preferred embodiment the conductivity cell measuring conductivity of the dialysate has an accuracy of +/−1% and the accuracy of volume measurement in the UF tank 24 may be ±1%. The worst case accuracy for dilution volume is estimated at 2 to 3%. If mixing is complete, this method can still achieve 1% accuracy on the desired conductivity. Greater accuracy of the quantity of water added to the dialysate solution flow path can be achieved by using a flow meter in the water line, or other suitable method if necessary, rather than measuring the volume in the UF tank 24. An accuracy of dialysate conductivity to within 1% of the desired or target level, as achieved by present invention, is a substantial improvement over the 5% guideline set forth by the AAMI (Association for the Advancement of Medical Instrumentation).

It will be further understood that an entire suite or collection of dialysate formulations may be required for preparation of difference dialysate solutions to treat a given dialysis patient population. The collection of vessels for the liquid acid and bicarbonate formulations will accordingly have varying amounts and compositions to form the basis for the suite of formulations. Excess chemicals (e.g., 5%) may be to each of the individual liquid acid and bicarbonate formulation vessels. The above dilution procedure is followed for every formulation when the solution is prepared.

Figure 2:
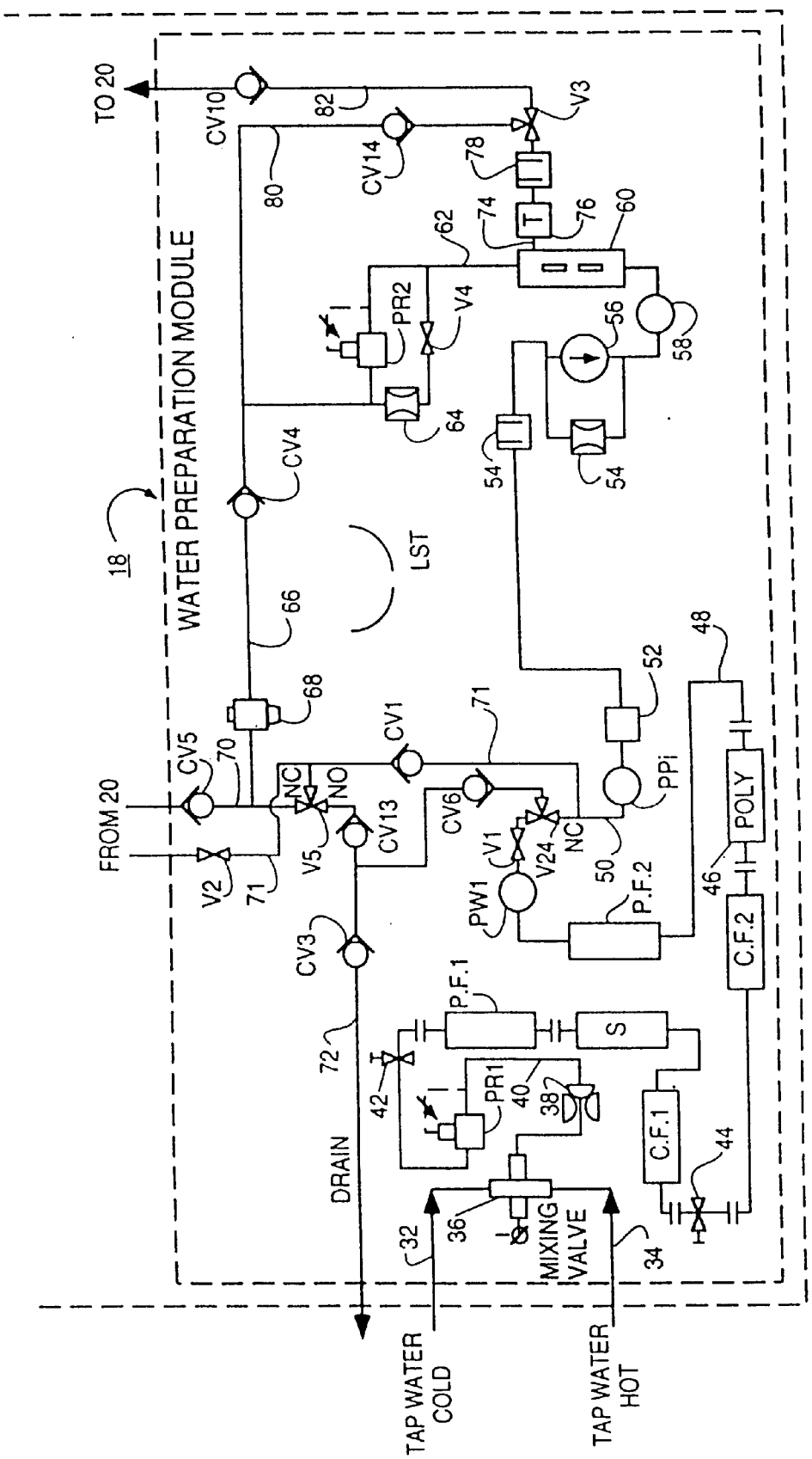
FIG. 2 is a more detailed schematic diagram of a water filtration module used to supply the dilution volume to the dialysate preparation module of FIG. 1, and FIGS. 3A and 3B are a more detailed schematic diagram of a presently preferred batch dialysate preparation module and extracorporeal circuit module, respectively, of FIG. 1 for use in performing the invention in a hemodialysis machine.
Figure 3A:
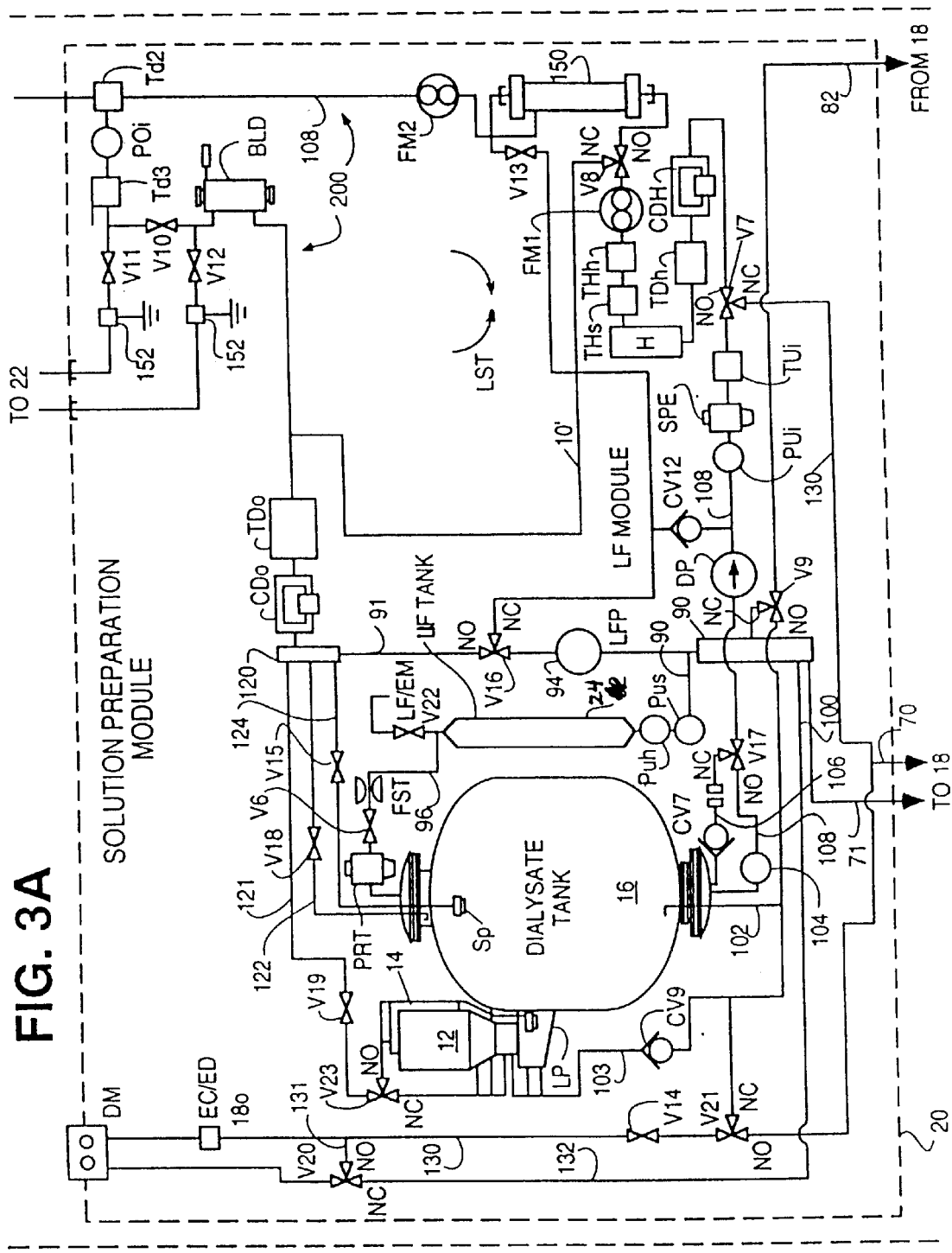
Figure 3B:
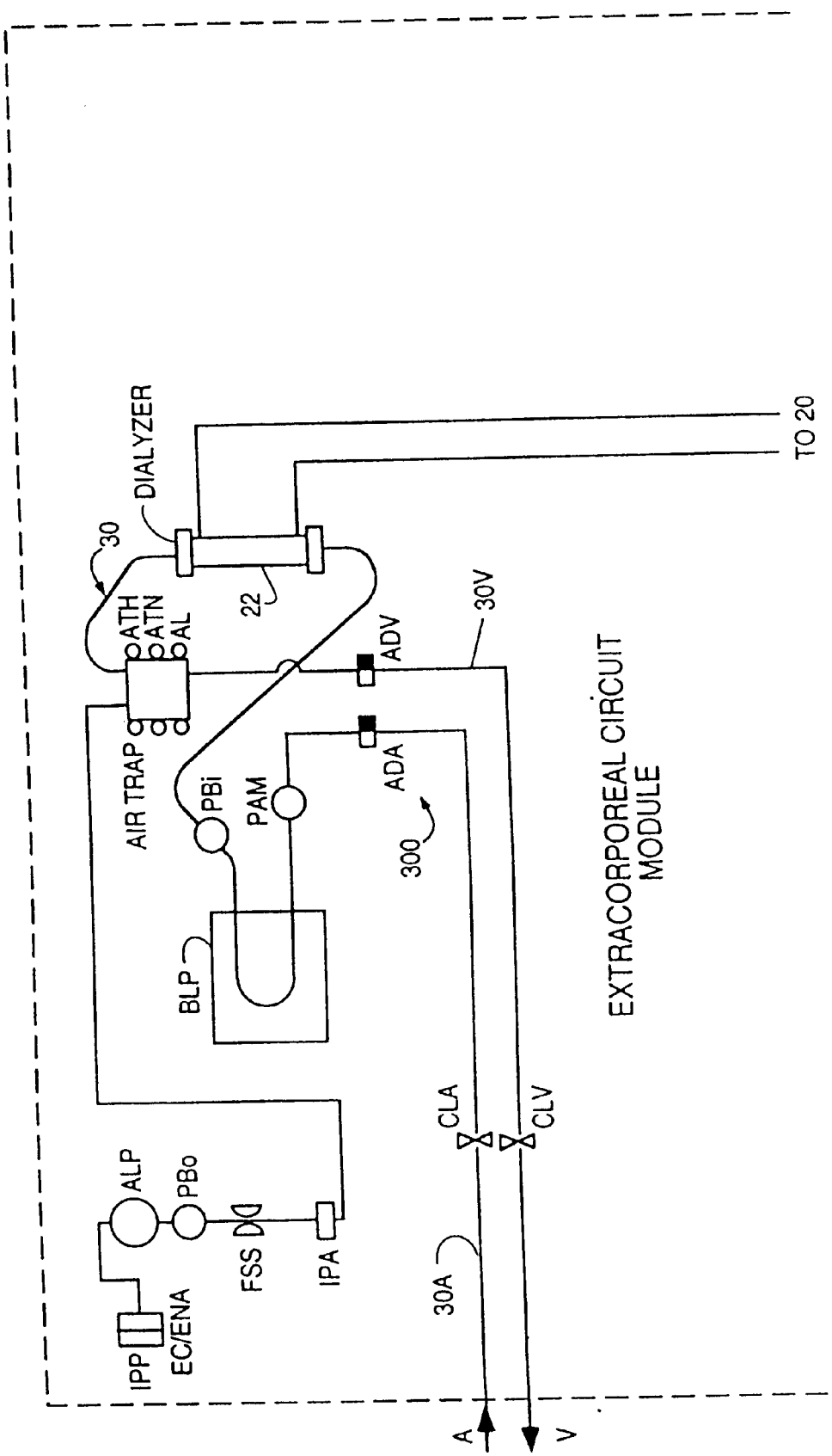

Detailed schematics of a preferred hemodialysis embodiment of the invention are shown in FIGS. 2 and 3. FIG. 2 shows schematically a preferred water preparation module 18 that prepares filtered water for the dialysis machine from incoming tap water, and supplies the water to the dialysate preparation module 20, shown in detail in FIG. 3.

Referring to FIG. 2, cold tap water is applied on a line 32 to a temperature controlled mixing valve 36, where it is mixed with hot water supplied on a line 34. The temperature controlled mixing valve 36 supplies water at a desired temperature (e.g., 30 degrees C) to the rest of the fluid circuitry. This circuitry includes a back flow preventer 38 in an inlet line 40, a pressure valve PR1, a shut off valve 42, a primary particulate filter PF1, an optional water softener S, and a primary carbon filter CF1. A valve 44 with a sample removal port is provided in the line 40. A secondary carbon filter CF2, a polyphosphate water conditioning and surfactant agent 46 and a secondary particulate filter PF2 are provided in line 48, which supplies water past water inlet pressure transducer PW1. Electrically activated valves V1 and V24 are placed in the inlet line 48. The normally closed port NC of valve V24 leads to a line 50 having a pressure sensor PPi, a thermistor 52, and an invasive conductivity cell 54, which supplies water to a pump 56. A flow constrictor 54 is placed across the inlet and outlet of the pump 56. The outlet line from pump 56 includes a pressure transducer PRi 68 which measures the pressure on the inlet of a Reverse Osmosis (RO) filter 60.

The feed side of the RO filter 60 includes a line 74 having a thermistor 76, a second invasive conductivity cell 78, a three-way valve V3 and an outlet line 82 supplying water to the dialysate preparation module 20. The reject side of the RO filter includes a line 62 having a valve V4, a flow constrictor 64, and a pressure regulator PR2. The line 62 and line 80 from valve V3 lead to a drain line 66 having a check valve CV4 and a pressure relief valve 68 with integral sample removal port 68. The drain line 66 meets with a drain line 70 from the dialysate preparation module 20 and leads to three-way valve VS. This line continues with a check valve CV 13, a second check valve CV 3 and leads to a drain line 72 leading out of the dialysis machine 10. Line 71 also leads to the water preparation module 19 via valve V2 and provides for introduction of hot water through lines 50, 74, 62, 80, 82 and 66 during hot water sanitization periods for the water preparation module 18.

It will thus be appreciated from FIG. 2 that incoming water on line 32 and 34 is treated for chlorine or chloramine by the carbon filters CF1 and CF2, treated for particulate matter by the particulate filter PF1, conditioned by the polyphosphate cartridge 46, and reverse osmosis filtered by RO filter 60. The feed water is supplied via line 82 to the batch dialysate preparation apparatus and the ultrafiltration tank in a dialysate preparation module 20 in a manner described in detail below.

FIG. 3 shows a presently preferred dialysate preparation module 20 in a detailed schematic diagram. Inlet RO filtered water on line 82 is supplied to a three way valve V9. The normally closed port NC on valve V9 leads to a line 90 supplying water to an ultrafiltration tank 92 (the same as UF tank 24 in FIG. 1). Two pressure sensors PUS and PUH measure the hydrostatic pressure and hence volume of fluid in the UF tank 92. A UF pump 94 pumps dialysate from the dialysate circuit via V16 into the UF tank to assist in mixing dialysate with water in the UF tank 92 as described above. The top of the UF tank is connected via line 96, a valve V6, and a pressure relieve valve PRT to the top of a dialysate preparation tank 16.

The dialysate preparation tank 16 receives the incoming RO water through valve V9 and inlet lines 100 and 102 at the bottom of the tank 16. A pair of batch dialysate chemicals vessels 12 and 14 and a loading platform LP are positioned against the side of the tank 16. A preferred loading platform apparatus LP, and the process and structures for automatically opening the vessels 12, 14 and adding the dialysate chemicals to the tank 16 are described at length in the above-referenced Kenley et al. U.S. Pat. No. 5,591,344.

The dialysate circuit 200 flow path includes outlet lines 108 and 106 from the bottom of the tank 16 which lead to three way valve V17. Line 106 is a degassing line. Line 108 has a pressure transducer 104 for measuring the volume of fluid in the tank 16. The valve V17 leads to a dialysate pump DP which pumps the dialysate from the tank 16 to the dialyzer 22 and back to the tank 16. In the dialysate line 108, the following components are placed in the fluid path:

PUi—a pressure transducer;
SPt—a sample removal port for allowing samples of fluid to be removed from the line 108;
TUi—a thermistor;
V7—a three-way valve connecting line 108 to line 130;
CDH—a noninvasive conductivity sensor for measuring the conductivity of dialysate in line 108, and sending readings to a host central processor;
TDH—a thermistor sending temperature readings to the host CPU, enabling temperature compensation for the conductivity readings;
H—a heater for heating the dialysate to the proper temperature, and water to a high level disinfection temperature during disinfection cycles of the machine;
THs—and THh—thermistors sending temperature readings to safety (backup) and host CPUs
FM1—a flow meter
V8—a three-way valve connecting line 108 with line 101.

A pyrogen filter 150 is placed in the dialysate line 108 to filter any pyrogens in the dialysate. A flow meter FM2 measures the flow rate of dialysate to the dialyzer 22. Thermistors Td2 and Td3 measure the dialysate temperature prior to entering the dialyzer 22. Pressure sensor Pdi measures the inlet dialysate pressure. Valves V10, V11, and V12 control the flow of dialysate into and out of the dialyzer 22. V11 is a bypass valve, and closes and V10 opens to divert dialysate away from the dialyzer. V12 closes to force dialysate through the dialyzer 22 membrane into the extracorporeal circuit 300. Ground contacts 152 electrically ground the dialyzer 22, isolating the patent's blood from any stray currents in the dialysate circuit. A blood leak detector BLD detects the presence of blood in the dialysate line 110 containing "old" dialysate. A dialysate temperate thermistor Tdo and a conductivity cell Cdo operate together to measure conductivity of the dialysate in the line 110.

The dialysate coming back from the dialyzer 22 in line 110 meets a manifold 120. Ordinarily, during dialysis, dialysate passes on line 122 past valve V18 into the top of the tank 16. During mixing, dialysate passes through line 124 having valve V15 and into a sprayer SP suspended within the tank 16. During dialysis, a specified quantity of dialysate and fluid from the patient is removed from the line 110 into a line 91 past valve V16 by the ultrafiltration pump 94 and pumped into the UF tank 92 in accordance with the ultrafiltration principles taught in the above-referenced Kenley et al. Patent, U.S. Pat. No. 5,591,344. A fourth line 121 is used to direct fluid (or water) via valve V19 to a three-way valve V23, which supplies water to the opening apparatus below the vessels 12 and 14. The normally open port of valve V23 leads to the sprayer within the loading platform LP. A drain line 103 drains fluid from the opening apparatus and conducts it to the drain line 70 via valve V21.

The operation of valves V9, V16 and the operation of the ultrafiltration pump 24 also can cause fluid from the ultrafiltration tank 92 to be pumped along a line 132 past valve V20 to a disinfection manifold DM. The disinfection manifold DM has two ports that receive the connectors at the end of the patient's arterial and venous lines after treatment. Line 132 supplies fluid to the arterial line 30A when the arterial line is connected to its port. Line 130 receives fluid from the venous line 30V when the venous lines 30V is connected to its port. Valve V14 and valve V20 provide a way for recirculating fluid through the arterial and venous lines 30A and 30B when the blood pump BLP of the extracorporeal circuit 300 is operative and the lines 30 are connected to their respective ports in the manifold DM. Line 130 is connected via a valve V21 to the drain line 70 of the water preparation module 18.

The reader is directed to the disclosure of the above-referenced Kenley et al. patent U.S. Pat. No. 5,591,344 for a more exhaustive discussion of the components and operation of the dialysate preparation module 20. The minor differences between the circuitry of FIG. 3 and the dialysate preparation module of the Kenley et al. patent are irrelevant for the purposes of describing the present dialysate conductivity adjustment and mixing invention. Similarly, a discussion of the various components of the extracorporeal blood circuit 300 are more fully set forth in the Kenley et at. patent, and will be omitted here since such details do not pertain to the present invention.

Alternative Method of Preparation of Dialysate Solution

An alternative method for preparation of a batch of dialysate solution from the liquid and bicarbonate formulations in vessels 12 and 14 will now be described in conduction with FIGS. 1 and 3A. The method described below is advantageous in that the mixing can be performed in a relatively short amount of time. Further, the method may optionally be practiced using the precise control over conductivity using the above dilution or "trimming" techniques enabled by slight overfilling of the bottles.

At the beginning of the process, both the main dialysate preparation tank 16 and the ultrafiltration tank 24 are empty, sanitized, and cleaned of endotoxins. The tanks 16 and 24 are empty.

First, the chemical vessel 12 containing a liquid acid formulation is opened and the contents added to the dialysate preparation tank 16. Then the acid is moved to the ultrafiltration tank 24, such as by operating the pump DP in the dialysate circuit to pump the liquid in the ultrafiltration tank 24. Then, the dialysate tank 16 is rinsed with 3–4 liters of reverse-osmosis (RO) filtered water and the resulting water/acid solution is moved to the ultrafiltration tank 24 until the tank 24 is full. This results in a dilution of the acid concentrate with 3–4 liters of RO water.

Then, the dialysate tank 16 is filled to approximately the base of the chemical loading platform LP with RO water. The vessel 14 containing the powdered bicarbonate chemical formulation, in which the contents thereof has heretofore remained isolated (i.e., the bottle closed), is then opened and the contents added to the dialysate preparation tank 16. Additional water is added to nearly fill the tank 16. The diluted acid solution in the ultrafiltration tank is then mixed with the bicarbonate solution. This may be accomplished by pumping the acid solution from the ultrafiltration tank 24 (with the ultrafiltration pump 94) and introducing the contents into the dialysate tank 16 via lines 120 and 122 while the dialysate tank's contents are being mixed with the dialysate pump DP. Once the ultrafiltration tank 24 is empty, the dialysate tank 16 is completely filled using RO water. The patent to Thomas M. Feldsien, et al., U.S. Pat. No. 5,690,821 describes a mixing technique that may be used during this process and the reader is directed to the '821 patent for further details.

During this mixing of the bicarbonate solution and the liquid acid solution, additional reverse-osmosis water may be added to the dialysate preparation tank and/or ultrafiltration tank to bring the conductivity down to the proper level.

The quantity of water to add can be determined using a variety of techniques. One way is to take advantage of the knowledge of the total system volume, and make an assumption as to quantity of the chemicals in the bottle, and/or take advantage of final conductivity data from the solution made the previous day. For example, the vessels may be assumed to contain a quantity of chemicals needed to prepare a 56 liter batch, and the calibration of the machine determined that the total system volume was 53.5 liters. Thus, in addition to completely filling the system with water, an additional 2.5 liters of water is added to the system with a commensurate amount directed to drain. The final solution should be within the desired range.

As a variation on the above procedure, the final conductivity from the previous batch of solution can be used. For example, the machine 10 may be used in a daily dialysis treatment therapy and the final conductivity values for each session are stored in a memory for the central computer control system. If the proper final conductivity for the batch of dialysate solution for the, same formulation is supposed to be, for example 13.6, and the previous batch had a conductivity of 13.4, then, assuming approximately the same chemicals are stored in the same bottles of the same lot, the next solution is prepared with slightly less volume of dilution fluid. The equations above can be used to adjust the volume of fluid to add in the dilution step.

After the dilution volume has been added the machine conducts a final conductivity check to confirm that the solution is within range. If the solution is out of range an alarm is sounded and dialysis does not proceed.

The dialysate that must be removed from the system, because of adding dilution water in excess of the system volume, can be used for other purposes in the machine. A preferred embodiment uses the excess solution by pumping the solution through the extracorporeal circuit and blood tubing set as an endotoxin rinse. Alternative uses could be for priming the extracorporeal circuit, conducting dialyzer clearance tests, pressure tests for determining the integrity of the extracorporeal circuit or connection of the arterial and venous lines to the extracorporeal circuit ports, as described in the pending patent application of Rodney S. Kenley, Ser. No. 09/140,483 filed Aug. 26, 1998, U.S. Pat. No. 6,044,691 incorporated by reference herein.

The above mixing procedure has some advantages and avoids some of the problems that can arise when a physiologic solution is being prepared from acid and bicarbonate components. With the above method, the bicarbonate is fully dissolved before the liquid acid solution is mixed with the bicarbonate solution. If you were to add the liquid acid when the bicarbonate is not fully dissolved or is highly concentrated, the resulting solution is unstable and loss of carbon dioxide gas from the tank can produce calcium precipitation at the bottom of the tank.

A variation on the above method can be practiced in which the chemical loading platform shelf LP is placed at the top of the tank 16. The acid is added to the tank first. Then the tank is filled up all the way, with a weak acid solution present in the tank. The resulting weak acid solution is then pumped through a cartridge containing the powdered bicarbonate formulation to dissolve the bicarbonate. Variations on this technique are described in U.S. Pat. Nos. 5,348,389 and 5,344,231, and the patent to Twardowski, U.S. Pat. No. 5,336,165, which are incorporated by reference herein.

Furthermore, by making use of the conductivity-concentration relationship, it is possible to calibrate the system volume automatically. The method consists of the following steps:

1. Add a known quantity of electically conductive chemical to the vessels 12 and 14, and follow the procedures described above to prepare a batch of dialysate solution in the tank 16. Then, circulate the solution in the dialsyate flow path in module 20.
2. Measure the conductivity of the resulting solution.
3. Calculate the calibrated system volume using the following equations $$V_{sys} = M/c. \tag{6}$$

and $$C = a_1 r + b_1 \tag{7}$$

where M is the mass in grams of the chemicals introduced into the system from the vessels 12, 14, $V_{sys}$ is the calibrated system volume, C is the resulting chemical concentration in grams/liter, r is the measured conductivity of the solution, $a_1$ is the linearity coefficient and $b_1$ is the linearity constant.

Specifically, by substituting for C from equation (7) in equation (6), the following result is obtained:

$$V_{sys}=M/(a_1 r+b_1) \quad (8)$$

Precise weight measurements of the chemicals and complete mixing of the chemicals in the flow path provide better than 1% accuracy in the volume measurement of the system. Therefore, this is an efficient way of performing the automatic calibration of the system volume. The calibration procedure can be performed once at the time of manufacture of the machine, or in the field periodically, such as whenever dialysate solution flow path components are replaced.

Many specific details concerning one possible implementation of the operation of the mixing of the dialysate solution, the construction of the opening apparatus for the dialysate chemical vessels, and other aspects of the embodiment of FIGS. 2 and 3 will be apparent from the above-referenced Kenley et al. U.S. Pat. No. 5,591,344, which is incorporated by reference herein. Presently preferred dialysate chemical formulations are described in the patent application of Dilip H. Shah et al., Ser. No. 08/712,424, filed Sep. 11, 1996, abandoned, also incorporated by reference herein.

Further, the present invention may be practiced in batch physiologic solution preparation systems that vary in terms of their fluid circuitry components and design from the embodiment described herein. The true scope and spirit of the invention is intended to encompass these types of modifications from the details of the presently preferred embodiments. Further, the term "module" is intended to refer to a collection of components that together perform a specified function, such as filter or treat water or prepare a batch of dialysate. The components in the "module" need not and often will not be housed in a discrete enclosure.

Further, as noted above, the invention may be practiced in a batch peritoneal dialysis embodiment in accordance with the principles described above. A vessel analogous to the ultrafiltration tank may be provided in fluid communication with the dialysate circuit for storing the volume of water to be introduced to the dialysate flow path. Alternatively, the water may be introduced directly into the dialysate without using a tank. Additional physiologic fluids that can be prepared in accordance with the disclosed methods are physiologic substitution fluids used in hemofiltration, and physiologic irrigation fluids used for surgical procedures, such as arthroscopic surgery. The true scope and spirit of present invention is defined by the appended claims, interpreted in light of the foregoing.

We claim:

1. A method of calibrating a dialysis machine to determine the volume of a dialysate flow path of said machine, said dialysate solution flow path including a dialysate preparation tank, comprising the steps of:

introducing a known quantity of electrically conductive chemicals into said dialysate preparation tank;

filling said dialysate solution flow path with water;

mixing said chemicals with said water to form a solution;

measuring the conductivity of said solution; and calculating said system volume ($V_{sys}$) according to the relation:

$$V_{sys}=M/(a_1 r+b_1)$$

where M is the mass in grams of said chemicals;

$a_1$ and $b_1$ are a coefficient of linearity and a constant of linearity, respectively, for said chemicals; and r is said measured conductivity of said solution.

2. The method of claim 1, wherein said method is performed at the time of manufacture of said dialysis machine.

3. The method of claim 1, wherein said method is performed after the time of manufacture of said dialysis machine and after said dialysis machine has been shipped to a place of use of said machine, and after a component of said dialysis flow path has been replaced.

4. The method of claim 1, wherein said electrically conductive chemicals comprise a batch quantity of a dialysis solution chemical or chemicals.

* * * * *